United States Patent
Neilson

(10) Patent No.: US 10,883,978 B2
(45) Date of Patent: Jan. 5, 2021

(54) METHOD AND DEVICE FOR CALIBRATION OF BIOLOGICAL FLUX

(71) Applicant: Agilent Technologies, Inc., Santa Clara, CA (US)

(72) Inventor: Andrew C. Neilson, Sunapee, NH (US)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 571 days.

(21) Appl. No.: 15/421,173

(22) Filed: Jan. 31, 2017

(65) Prior Publication Data

US 2018/0217126 A1    Aug. 2, 2018

(51) Int. Cl.
| | | |
|---|---|---|
| *G01N 33/497* | (2006.01) | |
| *B01D 63/08* | (2006.01) | |
| *B01D 69/10* | (2006.01) | |
| *B01L 3/00* | (2006.01) | |

(52) U.S. Cl.
CPC ......... *G01N 33/497* (2013.01); *B01D 63/088* (2013.01); *B01D 69/10* (2013.01); *B01L 3/50255* (2013.01); *B01D 2313/56* (2013.01); *B01L 2200/0694* (2013.01); *B01L 2200/143* (2013.01); *B01L 2200/148* (2013.01); *B01L 2300/0618* (2013.01); *B01L 2300/0663* (2013.01); *B01L 2300/0681* (2013.01); *B01L 2300/0829* (2013.01); *B01L 2300/0851* (2013.01); *B01L 2300/16* (2013.01); *B01L 2400/0478* (2013.01); *G01N 2033/4977* (2013.01)

(58) Field of Classification Search
CPC .... B01L 3/50255; B01L 63/088; B01L 69/10; G01N 33/497; G01N 33/00; B01D 69/10
USPC .......... 422/536, 552–553; 435/297.5, 305.2, 435/305.3, 535; 436/8, 133, 136, 178
See application file for complete search history.

(56) References Cited

U.S. PATENT DOCUMENTS

| | | | | |
|---|---|---|---|---|
| 4,296,205 A | * | 10/1981 | Verma | C12M 29/04 210/644 |
| 4,427,415 A | * | 1/1984 | Cleveland | B01L 3/50255 210/232 |
| 4,895,706 A | * | 1/1990 | Root | B01D 61/18 422/534 |
| 4,948,442 A | * | 8/1990 | Manns | B01L 3/50255 156/268 |
| 5,104,804 A | * | 4/1992 | Humphries | C12M 25/04 204/403.02 |
| 5,306,420 A | * | 4/1994 | Bisconte | B01D 61/18 210/143 |

(Continued)

FOREIGN PATENT DOCUMENTS

| | | |
|---|---|---|
| EP | 0596482 A1 | 5/1994 |
| EP | 2322913 A2 | 5/2011 |

OTHER PUBLICATIONS

Bader, A. et al, Xenobiotica 1998, 28, 815-825.*

(Continued)

*Primary Examiner* — Arlen Soderquist

(57) ABSTRACT

An apparatus for calibrating a flux analyzer comprises a first frame; a second frame; and a permeable membrane. The first frame and the second frame are connected or integrally formed. A method for calibrating a flux analyzer is provided which uses an artificial standard rather than a biological standard.

19 Claims, 3 Drawing Sheets

(56) References Cited

U.S. PATENT DOCUMENTS

| | | | | |
|---|---|---|---|---|
| 5,326,533 A * | 7/1994 | Lee | B01D 61/18 | 210/455 |
| 5,342,581 A * | 8/1994 | Sanadi | B01L 3/5025 | 422/552 |
| 5,462,874 A * | 10/1995 | Wolf | C12M 23/08 | 422/535 |
| 5,536,662 A * | 7/1996 | Humphries | C12M 25/04 | 204/403.02 |
| 5,602,028 A * | 2/1997 | Minchinton | C12M 25/02 | 210/615 |
| 5,958,762 A * | 9/1999 | Stoppini | C12M 23/04 | 435/297.5 |
| 6,043,027 A * | 3/2000 | Selick | B01L 3/5025 | 422/417 |
| 6,280,586 B1 * | 8/2001 | Wolf | G01N 33/54373 | 204/403.01 |
| 6,908,767 B2 * | 6/2005 | Bader | B01L 3/5025 | 435/286.1 |
| 7,112,443 B2 * | 9/2006 | Hajduk | G01N 7/10 | 422/504 |
| 7,156,996 B2 * | 1/2007 | Watzele | B01D 61/28 | 210/321.71 |
| 7,276,351 B2 | 10/2007 | Teich et al. | | |
| 7,611,630 B2 * | 11/2009 | Babcock | B01D 61/147 | 210/321.6 |
| 8,202,702 B2 | 6/2012 | Neilson et al. | | |
| 8,435,751 B2 * | 5/2013 | Zweigart | A61L 27/26 | 210/640 |
| 9,029,147 B2 * | 5/2015 | Colton | C12N 5/0657 | 435/377 |
| 9,850,457 B2 * | 12/2017 | Sarver, Jr. | C12M 23/22 | |
| 2002/0098593 A1 * | 7/2002 | Nelson | G01N 25/482 | 436/147 |
| 2002/0182720 A1 * | 12/2002 | Gevaert | C12M 25/04 | 435/288.4 |
| 2003/0124029 A1 * | 7/2003 | Webb | B01L 3/5025 | 435/287.2 |
| 2003/0186217 A1 * | 10/2003 | Bader | B01L 3/5025 | 435/4 |
| 2003/0219716 A1 * | 11/2003 | Avdeef | G01N 13/00 | 435/4 |
| 2004/0077075 A1 * | 4/2004 | Jensen | B01L 3/5027 | 435/297.2 |
| 2004/0195163 A1 * | 10/2004 | Watzele | B01D 61/28 | 210/321.72 |
| 2005/0054028 A1 * | 3/2005 | Teich | B01L 3/5085 | 435/29 |
| 2005/0063862 A1 | 3/2005 | Roscoe et al. | | |
| 2007/0037285 A1 * | 2/2007 | Ehret | B01L 3/502 | 436/34 |
| 2007/0087401 A1 * | 4/2007 | Neilson | G01N 33/5008 | 435/29 |
| 2007/0166816 A1 * | 7/2007 | Campbell | B82Y 30/00 | 435/288.4 |
| 2007/0205155 A1 * | 9/2007 | Babcock | B01D 61/147 | 210/644 |
| 2008/0014571 A1 | 1/2008 | Teich et al. | | |
| 2010/0124761 A1 | 5/2010 | Neilson et al. | | |
| 2010/0196871 A1 * | 8/2010 | Dodgson | A61D 19/022 | 435/1.1 |
| 2010/0216229 A1 * | 8/2010 | Kenney | C12M 23/08 | 435/303.1 |
| 2010/0261277 A1 * | 10/2010 | Colton | C12N 5/0657 | 435/377 |
| 2011/0226686 A1 * | 9/2011 | Maurer | A61M 1/1698 | 210/206 |
| 2011/0263020 A1 * | 10/2011 | Zweigart | A61L 27/26 | 435/396 |
| 2011/0275112 A1 * | 11/2011 | Sarver, Jr. | C12M 23/22 | 435/34 |
| 2014/0170671 A1 | 6/2014 | McGarr et al. | | |
| 2014/0186876 A1 | 7/2014 | Teich et al. | | |
| 2015/0005258 A1 * | 1/2015 | Khan | C07F 9/5442 | 514/119 |
| 2015/0343439 A1 | 12/2015 | Burroughs et al. | | |
| 2016/0022709 A1 * | 1/2016 | Khan | A61K 45/06 | 514/85 |
| 2016/0096173 A1 | 4/2016 | Teich et al. | | |
| 2016/0215267 A1 | 7/2016 | Kanamune et al. | | |

OTHER PUBLICATIONS

Schmitmeier, S. et al, Biotechnology and Bioengineering 2006, 95, 1198-1206.*
Schmitmeier, S. et al, Journal of Membrane Science 2007, 298, 30-40.*
Mauth, C. et al, Biotechnology Progress 2010, 26, 1724-1732.*
Extended European Search Report dated Jun. 1, 2018, Application No. 18150929.0, 7 pages.

* cited by examiner

METHOD AND DEVICE FOR CALIBRATION OF BIOLOGICAL FLUX

CROSS-REFERENCE TO RELATED APPLICATIONS

None.

FIELD OF THE INVENTION

This invention relates to methods and devices for improved calibration of a flux analyzer, such as an instrument that measures biological flux.

BACKGROUND

Living cells typically consume oxygen (O2) from their surrounding environment and release metabolic byproducts, such as carbon dioxide (CO2), lactate, and various other metabolic byproducts. Flux analyzers allow one to measure the oxygen consumption rate (OCR), extracellular acidification rate (ECAR), CO2 production rate (CPR), and/or other biological flux parameters. Such measurements can provide valuable information regarding the metabolic processes carried out by these living cells.

One known method of measuring the OCR and ECAR of living cells is by measuring flux of O2 and H+ generated by these living cells in a wellplate using a set of fluorescent sensors. An example of an analyzer using fluorescent sensors to detect flux of O2 and H+ is the Seahorse flux analyzer, which is generally described in U.S. Pat. Nos. 7,276,351 and 8,202,702. The fluorescent sensors measure the intensity of fluorescent signals over time. For a sample containing living cells, those signals over time will be proportional to the rate of production or consumption of O2 molecules and H+ ions consumed or produced by the metabolism of the cells. This data is used to calculate the flux of O2 molecules and H+ ions consumed and produced by the living cells.

Problems connected with flux analyzers and flux measurements include a lack of standardization and unavailability of precise calibration references. Because flux is measured over time rather than at steady state conditions, the rate of chemical diffusion or permeation into the sensor and surrounding medium can vary between analytes creating a complex and dynamic measurement environment. Currently, to address these problems, flux measurement systems typically apply complicated algorithms to compensate for the various rate constants associated with each analyte. These rate constants are empirically derived based on biological references. Final verification of system performance is commonly done using biological standards that contain a known content of cells of a certain type; for example, a well characterized, immortalized, rodent, skeletal muscle fibroblast cell line (C2C12) is frequently used as a standard. These cell lines are maintained in culture in a level 2 biolab prior to use. In preparation for the assay the cells are trypsinized, counted and seeded into a well plate. The seeding quantity is controlled so that 24 hrs post seeding the cell population has grown to a measureable confluencey and is ready for use in the instrument. Because the cells continue to grow/expand after seeding the timing of the assay is critical to attain reproducible results. In addition, cell lines are inherently variable and subject to variability caused by passage, genotype, culture conditions. Because of these variables the typical reproducibility between wells, between assays often exceeds 20% cv. The variability of biological standards diminishes their capability of being suitable standards to use for verifying the performance of the flux measurement system.

Other methods for generating flux within a wellplate include the use of enzymes/catalysts such as glucose oxidase (GOx), sodium sulphate, or redox reactions. These methods have been previously used but are also subject to variability and complexity. For example; a typical enzymatic reaction is dependent on two or more compounds reacting to generate the desired signal. The reactions of the two compounds is concentration dependent, thus flux is variable (nonlinear) as the catalyst is consumed as part of the reaction. Additionally, these methods are difficult to tune in terms of a rate constants and become complex when more than one flux is desired. For such a method to replicate biological activity, reaction components would need to be adhered to the bottom of the plate, be linearly catabolized, at a controllable rate. These needs make this is a difficult and complex assay.

In summary, there is a need for better standards such as devices that do not rely on cells to be used to calibrate the performance of a flux analyzer.

DETAILED DESCRIPTION OF EMBODIMENTS

The term "flux" as used herein means change of a parameter as a function of time. The change may be expected due to consumption or reaction of a reactant represented by the parameter.

Figure 1A:
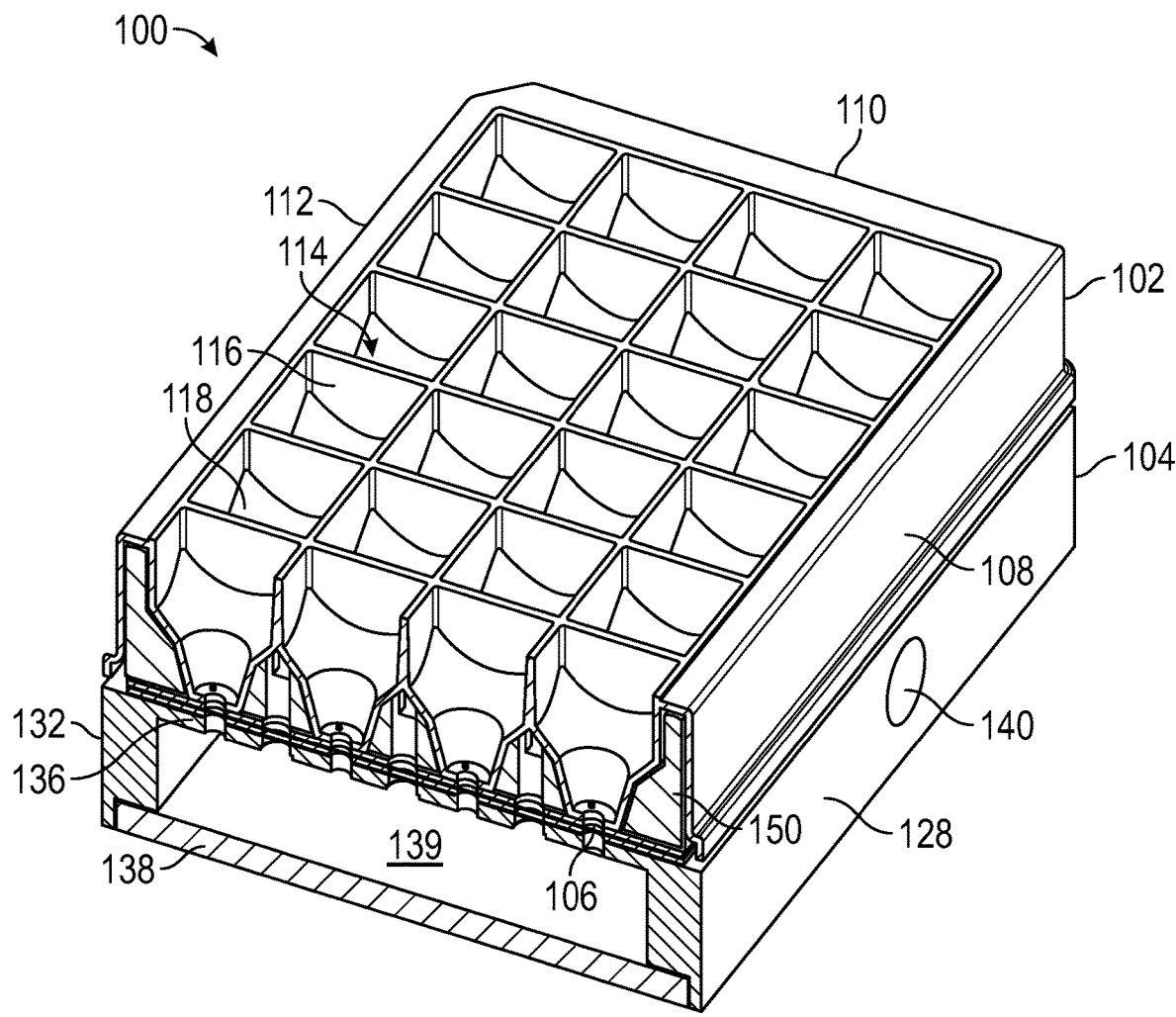
FIG. 1A is a cross-sectional view of one embodiment of a calibration apparatus of the present disclosure.
Figure 1B:
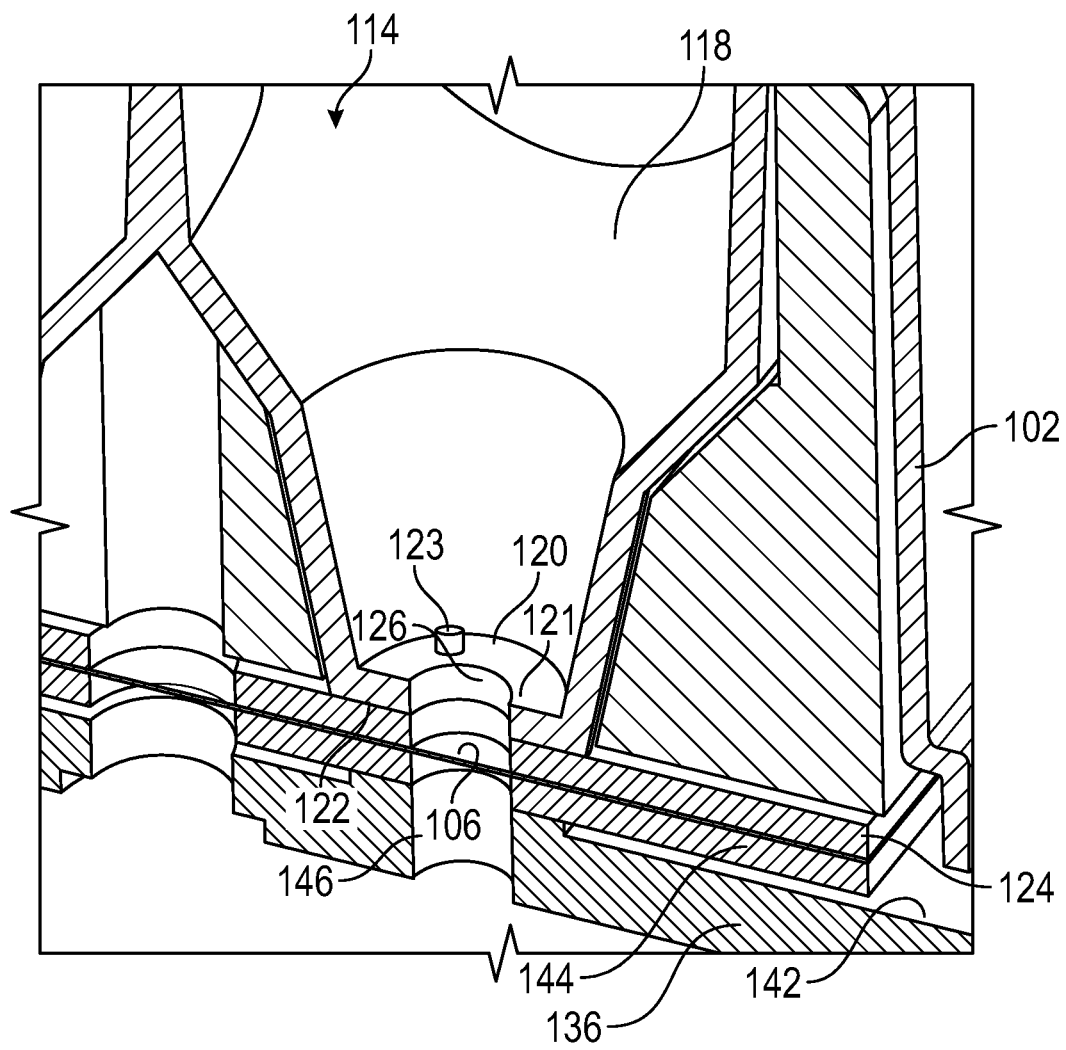
FIG. 1B is an enlarged cross-sectional view of a well of the calibration apparatus of FIG. 1A.

Referring now to FIGS. 1A and 1B, the flux block of the present disclosure is generally indicated by numeral 100. The flux block 100 includes: (1) a first frame 102; (2) a second frame 104; (3) and a selectively permeable membrane 106. In this embodiment, the first frame 102 of the flux block 100 and the second frame 104 of the flux block 100 are connected or integrally formed. For example, the flux block 100 can be formed from two or more separately formed sections (such as halves) that are suitably connected. The frames can have physical mating surfaces that permanently or removably interlock, such as where the edges snap together. Alternatively, the frames can be connected to each other by an adhesive or by soldering together.

More specifically, the first frame 102 includes a plurality of walls, including: (1) a first wall 108; (2) a second wall 110; (3) a third wall 112; and (4) a fourth wall (not shown in cross-sectional view). The walls of the first frame 102 include inner and outer surfaces. In certain embodiments, the first frame 102 defines a multi-well microplate or well plate. The plurality of walls of the first frame 102 partially encloses a plurality of wells 114. In certain embodiments, the plurality of wells 114 of the first frame 102 is disposed in four different columns and six different rows. Thus, the first frame 102 in this embodiment comprises twenty-four wells. The plurality of wells 114 can be conical or partially conical.

In certain embodiments, the plurality of wells 114 of the first frame 102 can be disposed in a different number of columns, a different number of rows, or a combination thereof. For example, another embodiment of the flux block 100 of the present disclosure can include a well plate including a plurality of wells 114 that are disposed in eight different columns and twelve different rows. Thus, this alternative embodiment of the well plate can include ninety-six wells. Yet another embodiment of the flux block comprises a single row of wells, for example, a single row of eight, 12, 16 or 24 wells. Yet another embodiment of the flux block comprises 16 different columns and 24 different rows. Thus, this alternative embodiment of the well plate can include 384 wells.

FIG. 1B illustrates a closer view of a single well 114 of the first frame 102 of the flux block 100, as well as its relation to a membrane 106 and a second frame 104. The walls 116 of this well 114 define a well void 118 configured to hold a volume of a suitable liquid sample(s). The walls 116 of the well 114 include inner and outer surfaces. The well 114 is configured to receive a plunger or other sensor, as further described below.

The flux block 100 of the present disclosure can include a filler 150. It should be appreciated that the filler 150 can be optional. The filler 150 can be made of the same material as the first frame 102 and/or the second frame 104. The filler 150 can also be made of other suitable material. The filler 150 should not interfere with the operation of the flux block 100.

The well 114 includes a well base 120. The well base 120 of the well 114 includes a first surface 121 and a second surface 122. The second surface 122 engages a first separator 124. The well base 120 and the first separator 124 each has an opening, and together they define a well opening 126. The well opening 126 allows CO2, O2, and/or other gas or liquid molecules to move in and/or out of the well void 118 of the well 114. In certain embodiments, liquid and or solid molecules can move through the well opening 126 to further move in and/or out of the well void 118 of the well 114.

In certain embodiments, the first surface 121 of the well base 120 has an uneven surface, and might be slightly raised in its outer perimeter than its inner perimeter. In certain embodiments, a sensor stop 123 extends from the first surface 121 of the well base 120 of the well 114. The sensor stop 123 is configured to engage a plunger when the plunger is seconded into the well void 118 of the well 114. Alternatively or additionally, a raised portion of first surface 121 may engage a sensor or plunger so as to prevent it from contacting a lower portion. More details regarding the use of the sensor/plunger are discussed below. In certain embodiments, the flux block 100 of the present disclosure can include one or more sensor stops 123 connected to and extending from the first surface 121 of the well base 120 of the well 114. In certain embodiments, the one or more sensor stop 123 can be defined by the inner surfaces of the well walls 116 of the wells 114. The one or more sensor stop 123 can be angled or sloped. Certain embodiments of the flux block 100 of the present disclosure can include one or more stop sensor 123 that lie in a step-like manner rather than being sloped or angled. Thus, the top surfaces of the one or more sensor stop 123 can be parallel to the top surface 121 of the well base 120 of the well 114.

Each of the wells may have a top portion with an opening having an area A1 as well as a bottom portion that may be cylindrical or square having an area A2, and the well may be defined by a tapered sidewall. A2 can be significant smaller than A1. A seating surface may be provided to act as a positive stop for sensors disposed on barriers. This seating surface enables the creation of a localized reduced volume of medium, as discussed in U.S. Pat. No. 7,276,351, incorporated by reference herein. In an embodiment, the seating surface may be defined by a plurality of raised dots, e.g., three dots, on a bottom surface of a well. The well areas and depths can be any dimension and may be preferably selected from an area A1 of 40 to 60 mm$^2$, alternatively 50 mm$^2$, an area A2 of 9 to 15 mm$^2$, alternatively 11.4 mm$^2$, and a depth of the wells may range from 1 to 16 mm or more, preferably about 15 mm; embodiments having those dimensions include plates comprise a single column or row of wells, and plates comprising 24 or 96 wells. In another embodiment, where the plate comprises 384 wells, and the well areas A1 and A2 and depths are the same as above, or proportional to the above numbers. Preferably, the wells are spaced equally from each other. Each of the wells in the microwell plate can have substantially the same dimensions or can have varying dimensions.

The second frame 104 includes a plurality of walls, including: (1) a first wall 128; (2) a second wall (not visible); (3) a third wall 132; (4) a fourth wall (not shown); (5) a fifth wall 136; and (6) a sixth wall 138. In this embodiment, the first wall 128 defines an inlet/outlet port 140 configured to receive a tube (not shown). It should be appreciated that certain embodiments of the flux block 100 of the present disclosure can include other suitable walls of the second frame 104 that define the inlet/outlet port 140. The walls of the second frame 104 include inner and outer surfaces. The sixth wall 138 can be removed to clean the flux block 100. The sixth wall 138 is removable from the second frame for suitable purposes such as clearing or repair.

In certain embodiments, the walls of the second frame 104 define a chamber 139 configured to hold a volume of suitable substance, such as CO2, O2, or a combination thereof. It should be appreciated that the chamber 139 can hold a volume of other substances, and the chamber can be adapted for holding such substances, such as by having a coating on its surfaces. It should further be appreciated that certain embodiments of the flux block 100 of the present disclosure can include walls of the second frame 104 that define a chamber 139 configured to hold a volume of suitable liquid sample(s), other suitable gaseous sample(s), or a combination thereof. The chamber can be divided into a plurality of subchambers and the frame can have different inlet-outlet parts for different subchambers.

The first surface 142 of the top wall 136 engages the second separator 144. The top wall 136 and the second separator 144, if present, define a chamber opening 146 that is aligned with the well opening 126. The chamber opening 146 and the well opening 126 are sufficiently aligned or concentric to allow CO2, O2, and/or other molecules to move in and/or out of the chamber 139 of the second frame 104 and into the well void 118.

The selectively permeable membrane 106 is configured to allow one or more substances to permeate across the permeable membrane 106, where those substances constitute or cause a flux which is measured by a flux analyzer. For example, the membrane may permit CO2, O2 or both to pass from one side of the membrane to the other. The selectively permeable membrane also acts as a barrier to one or more of water, other solvents, and other molecules. Generally, the permeable membrane prevents bulk movement of liquid in the wells into the chamber. As illustrated in FIG. 1B, the selectively permeable membrane 106 is held between the first separator 124 and the second separator 144. The first separator 124 and second separator 144 are configured such that the permeable membrane 106 does not generally move when positioned between the second surface 122 of the well base 120 of the well 114 and the first surface 142 of the fifth wall 136 of the second frame 104. The permeable membrane 106 acts as a boundary between the well voids 118 of the wells 114 and the chamber 139 of the second frame 104.

In certain embodiments of the flux block 100, the first separator 124 and the second separator 144 are configured such that when positioned between the first frame 102 and the second frame 104, the permeable membrane 106 is equidistant from the first surface 142 of the top wall 136 of the second frame 104 and the second surface 122 of the well base 120 of the well 114. In certain embodiments of the flux block 100 of the present disclosure, the first separator 124 and the second separator 144 can be configured such that when positioned between the first frame 102 and the second frame 104, the permeable membrane 106 is positioned other suitable distances from the first surface 142 of the top wall 136 of the second frame 104 to the second surface 122 of the well base 120 of the well 114. The separators and frames can have alignment indicia to ensure proper alignment. Furthermore, the permeable membrane 106 is a boundary between the well voids 118 of the wells 114 and the chamber 139 of the second frame 104.

In certain embodiments, the flux block 100 of the present disclosure does not include the first separator 124 and the second separator 144. In such embodiments, the selectively permeable membrane 106 engages the first surface 142 of the top wall 136 of the second frame 104 and the second surface 122 of the well base 120 of the well 114. In certain embodiments, the membrane extends across the face of the second frame 104 closest to the first frame 102. In such embodiments, the membrane 106 is a boundary between the well voids 118 of the wells 114 and the chamber 139 of the second frame 104. It should further be appreciated that the membrane 106 can be integral with either or both of the first frame 102 and the second frame 104. The membrane can be a single sheet that extends over substantially the whole surface of the first frame and/or second frame, or it can be in discrete patches that cover the well openings.

The flux block 100 of the present disclosure can be formed from a molded plastic, such as polystyrene, polypropylene, polycarbonate, or other suitable material. The bottoms of the wells may be opaque or reflective so that a sensor in the well collects light emitted or reflected by the contents in the well, or the well bottoms may be transparent to allow light to pass through those bottoms. In certain embodiments, the sides of the wells are opaque to reduce optical cross-talk or light contamination from one well to another. In some embodiments, e.g., for use with luminescence measurements, the wells may be white or reflective.

In certain embodiments, the permeable membrane 106 is a polymethylpentene film, such as a TPX film. Alternatively, the permeable membrane 106 can be polystyrene. It should further be appreciated that certain embodiments can include a selectively permeable membrane made of other suitable materials. In some embodiments, the membrane is removable from the apparatus, so that it can be replaced, thereby rejuvenating the calibration apparatus.

The flux block 100 of the present disclosure is designed for use in calibrating a well-based analytical system running a calibration application, such as an optical system or a flux analyzer. In some embodiments, a method of using the flux block of the present disclosure to calibrate a flux analyzer includes: filling the chamber of the second frame with a known $CO_2$ concentration, such as 100%; filling the well voids of the wells of the first frame with a buffer solution having a known $CO_2$ concentration, such as 0%; and measuring the change in concentration of an analyte such as $CO_2$ or $O_2$ or hydrogen ions over a period of time. In some embodiments, the method further comprises assessing whether the flux analyzer passed or failed. In some embodiments, the method further comprises comparing the measurements to one or more criteria and determining if the measurements meet the criteria; in those embodiments, the criteria can be a single value or a range of values. In some embodiments, the method further comprises assessing applying a correction factor to the analyzer or for further calibration.

More specifically, the method can comprise connecting a tube (not shown) to the inlet/outlet port 140 of the first wall 128 of the second frame 104. $CO_2$ molecules travel through the tube and into the chamber 139 of the second frame 104, thus purging the chamber 139 of the second frame 104 with 100% $CO_2$. In other words, the partial pressure of $CO_2$ in the chamber 139 is 100%. The partial pressure of $O_2$ in the chamber 139 of the second frame 104 is 0%. Upon purging the chamber 139 with 100% $CO_2$, the tubing apparatus is removed from the inlet/outlet port 140. A seal (not shown) covers the inlet/outlet port 140 by engaging the outer surface of the first wall 128 of the second frame 104. The seal allows the chamber 139 of the second frame 104 to contain the $CO_2$ molecules so that no $CO_2$ leaves the chamber 139 and that no other gaseous or liquid sample(s) enter the chamber 139.

The method further includes filling the well voids 118 of the plurality of wells 114 of the first frame 102 with a suitable volume of a test solution, such as a buffer solution having a pH of 7.4. The well voids 118 can hold a volume of other suitable liquid sample(s) and/or a volume of media about live cells. The method further includes measuring changes or flux in one or more parameters such as $CO_2$ while allowing the buffer solution to equilibrate under ambient conditions. The ambient conditions generally include conditions of partial pressures of gases being approximately 21% $O_2$ and 0.03% $CO_2$. By equilibrating under ambient conditions, the buffer solution equilibrates to include a partial pressure of $CO_2$ that is less than the 100% partial pressure of $CO_2$ in the chamber 139 of the second frame 104. This difference in partial pressure of $CO_2$ creates a concentration gradient of $CO_2$ across the permeable membrane 106. Thus, so long as there is a greater concentration of $CO_2$ in the chamber 139 of the second frame 104 than there is in the well voids 118 of the wells 114 that include the buffer solution, $CO_2$ will continue to move across the membrane. Furthermore, while the buffer solution equilibrates under ambient conditions, a concentration gradient of $O_2$ forms. Thus, there is a greater concentration of $O_2$ in the well voids 118 of the wells 114 that include the buffer solution than there is in the chamber 139 of the second frame 104 that includes a 0% partial pressure of $O_2$.

When the concentration gradients described above form between the chamber 139 of the second frame 104 and the well voids 118 of the wells 114 of the first frame 102, $O_2$ molecules and $CO_2$ molecules move down their concentration gradients. In other words, the molecules of each move from an area of higher concentration to a second concentration. In such case, the $CO_2$ moves from the chamber 139 of the second frame 104 to the well voids 118 of the wells 114. More specifically, $CO_2$ molecules move through the chamber opening 146. The $CO_2$ molecules further permeate across the permeable membrane 106. The $CO_2$ molecules further travel through the well opening 126 of the well 114, where the $CO_2$ molecules further solubilize in the buffer solution in the well voids 118 of the wells 114 of the first frame 102. The $O_2$ molecules move from the well voids 118 of the wells 114 to the chamber 139 of the second frame 104. More specifically, $O_2$ molecules move through the well opening 126 of the well voids 118 of the wells 114. The O2 molecules further permeate across the permeable membrane 106. The O2 molecules further travel through the chamber opening 146 of the chamber 139 of the second frame 104 and fill the chamber 139, thus increasing the O2 partial pressure in the chamber 139 of the second frame 104. The changes or flux of the O2 molecules and the CO2 molecules in the wells during the time period of equilibration can be calculated with a high degree of confidence, as explained in more detail below. Accordingly, the concentration of O2 molecules and CO2 molecules can be measured during equilibration, and the measured values can be compared to calculated values, and the accuracy of the analyzer can be determined. If the measured values are different from the calculated values, corrective action can be taken. The corrective action may be adjusting the analyzer, applying a correction factor to the existing measured values and/or future measured values, or cleaning or replacing sensors. In this way, the analyzer is calibrated.

As CO2 molecules solubilize in the buffer solution, the CO2 molecules undergo the following reaction:

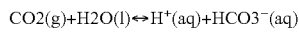

$$CO_2(g) + H_2O(l) \leftrightarrow H^+(aq) + HCO_3^-(aq)$$

In other words, the CO2 molecules react with the water (H2O) molecules in the buffer solution to form hydrogen ions or H+ ions. The formation of H+ ions causes the pH of the solution to decrease.

Figure 2:
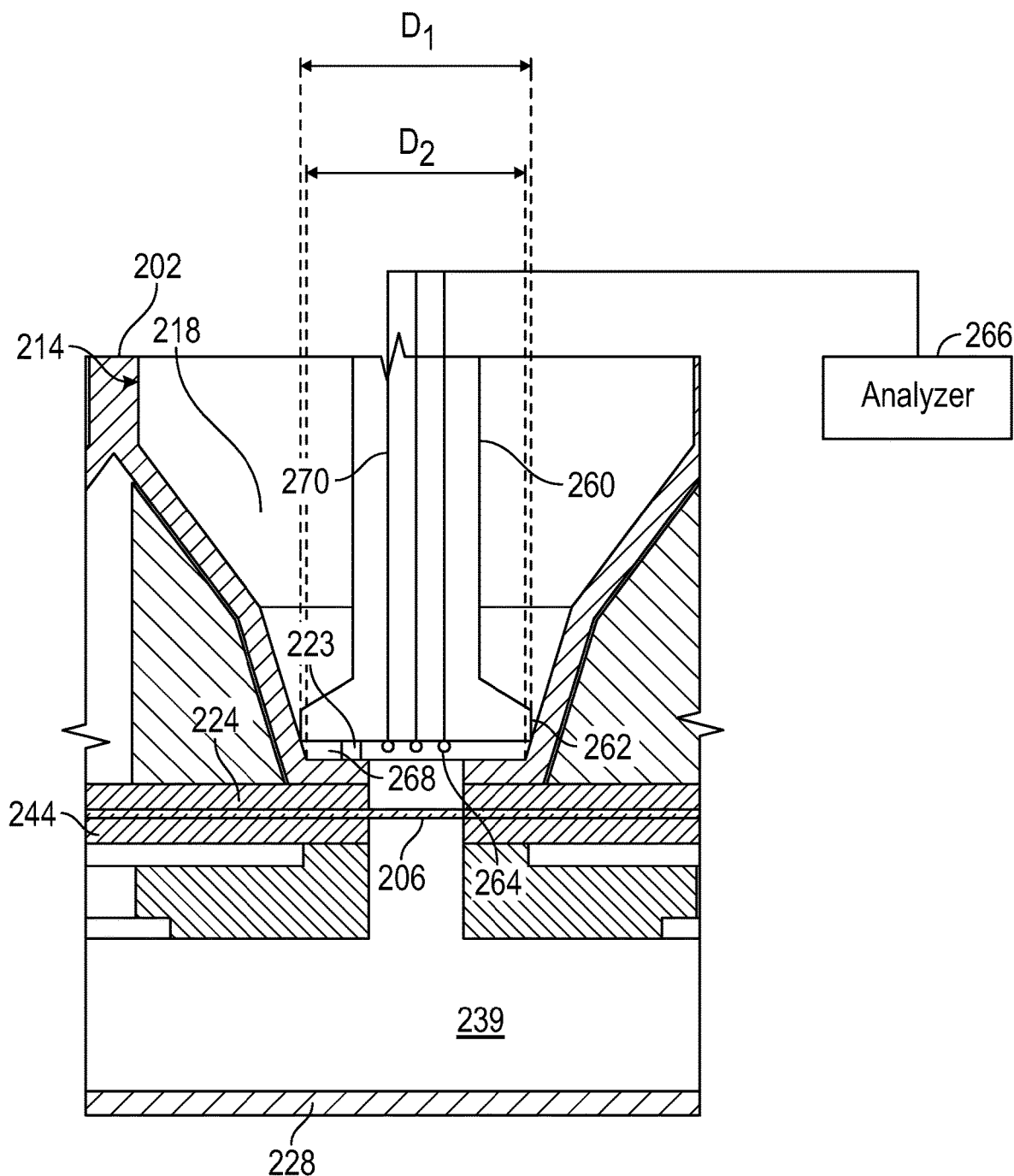
FIG. 2 is an enlarged cross-sectional view of a well of a calibration apparatus receiving a plunger to measure the flux rate of two analytes.

In certain embodiments, the method of measuring the change in concentration of O2 molecules and H+ ions and further calculating the flux of each analyte includes sending a plunger 260 into the well voids 218 of the wells 214 of the first frame 202. The plunger 260 comprises (e.g., contains, holds or supports) one or more sensors 264. FIG. 2 illustrates an embodiment of this process and apparatus in one well void 218 of a first well 214 of the first frame 202. In this embodiment, the permeable membrane 206 engages the first separator 224 and the second separator 244.

The plunger 260 extends from a manual or automatic actuator or other support. A barrier 262 is disposed at one end of the plunger 260. One or more sensors 264 are disposed at the distal end of the barrier 262 of the plunger 260. An example of a sensor is a fluorescent indicator, such as an oxygen-quenched fluorophore, embedded in an oxygen permeable substance, such as silicone rubber. The fluorescent indicator provides a fluorescent signal which is dependent on the presence and/or concentration of a constituent in the well. Other types of known sensors may be used, such as electrochemical sensors, ISFET sensors, and amperometric sensors such as the Clark electrode, for example.

In certain preferred embodiments, the one or more optical sensors include fluorescent sensors. The fluorescent sensors are configured to detect the intensity of fluorescent signals that are proportional to the rate of change in concentration of O2 molecules and H+ ions in the buffer solution over a period a time. The one or more sensors 264 communicate electrically via fiber optics or wires 270 with a system 266 that includes a processor running a calibration procedure. The calibration procedure is programmed to calibrate the system 266, using data (such as measured flux) collected, measured, or determined by the one or more sensors 264 in sensing communication with the analytes in the buffer solution in the well void 218 of the well 214.

In some embodiments, upon automated actuation, plungers 260 descend into the well voids 218 of the first frame 202. A single plunger descends into a given well, and the plungers can be precisely spaced so as to align with the locations of wells in a standard well plate, such as a standard 24-well plate, 96-well plate, or 384-well plate. The barrier 262 of the plunger 260 engages the sensor stop 223. Engagement of the barrier 262 of the plunger 260 and the plunger stop 223 of the well 214 defines a micro-well 268 having a reduced volume of media. In this embodiment, the micro-well 268 holds a reduced volume of buffer solution carrying out the chemical reaction(s) described above or other reactions. In some embodiments of the flux block 100 of the present disclosure, the micro-well 268 is configured to hold a volume of less than 10 microliters of buffer solution. This volume may be defined by the area of the bottom of the wells (for example, 11.4 mm$^2$) and the height of the stop barriers, for example, 0.2 mm). In certain embodiments, the micro-well 268 can be configured to hold a volume greater than 10 microliters of buffer solution or other suitable liquid sample (s). The micro-well 268 of this volume allows the one or more sensors 264 to measure the change in concentration of the O2 molecules and H+ ions over a period of time as O2 molecules move from the micro-well 268 to the chamber 239 of the second frame 228 and CO2 molecules move from the chamber 239 of the second frame 228 to the micro-well 268 to subsequently undergo the chemical reaction described above. The micro-well 268 of this volume further enhances measuring sensitivity. It should be appreciated that the micro-well 268 can be defined by moving the first frame 202 toward a stationary plunger such that the barrier of the stationary plunger or other support or arrangement of the sensor engages the sensor stops of the well 214 of the first frame 202. The sensor stop is optional, and any arrangement where the sensor is positioned at a desired height above the sample may be used.

Upon defining the micro-well 268, the one or more optical sensors 264 detects changes in fluorescent signals that are proportional to the rate of change in concentration of the O2 molecules and H+ ions in the micro-well 268 of the well 214 over a period of time. The one or more sensors 264 send data representing the change in these concentrations to the analyzer system 266 via the wires or fiber optics 270. The processor running the calibration application receives this data and measures the flux of each analyte. The processor further calibrates the optical analyzer 266 using: (1) the measured flux rate of each analyte; and (2) a correction factor programmed into the calibration procedure. Further detail on the use of a plunger is provided in U.S. Pat. No. 7,276,351, incorporated by reference herein.

In certain embodiments, the diameter of the wells 214, and particularly the diameter D2 (as shown in FIG. 2) at the bottom of the wells 214, of the flux block 100 of the present disclosure is slightly smaller than the diameter D1 (as shown in FIG. 2) of the barrier 262 of the plunger 260 such that the barrier 262 defines a boundary between the volume of the micro-well 268 and the remaining volume of the well void 218 of the well 214 when the barrier 262 engages the stop barrier 223 of the well 214.

In certain embodiments, the flux block 100 of the present disclosure can be configured to maintain a desired flux rate (Q) over a period of time of each analyte as each analyte moves across the permeable membrane. More specifically, the variables in the following equation can be adjusted such that a desired flux rate of each analyte is maintained: (1) a thickness of the permeable membrane (t); (2) a surface area of the permeable membrane (A); (3) a differential concentration of gas and/or liquid samples across the permeable membrane (dP1); (4) a gas pressure of the gas sample in the chamber of the second frame (dP2); and (5) a permeation coefficient of the permeable membrane (K). These variables can be adjusted and used in the following equation to maintain a desired flux rate of each analyte that moves across the permeable membrane.

$$Q = \frac{KAdP1dP2}{t}$$

In certain embodiments of the flux block 100 and calibration method of the present disclosure, the desired flux rate for O2 molecules is approximately 100-150 picomoles/min. Membrane parameters, such as the thickness and the material from which the membrane is made, may be selected so that the membrane will have a desired flux rate under its contemplated conditions of use (which include the pressure of test fluid (dP1) and partial pressure of the substance such as CO2 (dP2) which will pass through the membrane at the desired flux rate), dP1 is in units of psi and dP2 is a percentage. For a membrane of polymethylpentene material, contemplated for use in a flux block where the test fluid is 100% CO2 gas, the thickness will generally range from 50 um to 150 um and the area will generally range from 1 mm$^2$ to 5 mm$^2$. For a membrane of polystyrene under the same conditions, the thickness will generally range from 5 um to 15 um and the area will generally range from 1 mm$^2$ to 5 mm$^2$. The area of the well openings may be selected so as to determine the area of the membrane.

Certain embodiments of the flux block 100 of the present disclosure can be configured to allow the delivery of carbon sources, such as glucose, amino acids, fats, and active agents into the chamber 139 of the second frame 104, the well void 118 of the well 202, the sub-well 216 of the well 202, or a combination thereof. It should further be appreciated that certain embodiments can be configured and/or used to control environmental conditions of a bioreactor, such as the partial pressure of O2, the pH, etc. of liquid and/or gaseous samples.

Certain embodiments of the flux block 100 of the present disclosure can be configured to measure the flux rate of other suitable analytes, such as a dissolved gas (e.g., O2, CO2, NH3), an ion (e.g., H+, Na+, K+, Ca++), a protein (e.g., cytokines, insulin, chemokines, hormones, antibodies), a substrate (e.g., glucose, a fatty acid, an amino acid, glutamine, glycogen, pyruvate), a salt, and/or a mineral. The constituent may be extracted from the media by at least a portion of cells. The constituent may be secreted into the media by at least a portion of the cells.

It should further be appreciated that certain embodiments of the flux block 100 of the present disclosure can be formed or made of two or more, such as two separate, detachable parts including: (1) a first frame; and (2) a second frame. The first frame and the second frame, respectively, include a first and second attachment mechanism that respectively allows the first frame to be (permanently or removably) attached to the second frame and vice versa.

The present disclosure also provides kits comprising one or more flux blocks sealed in a foil bag. It has been found that flux blocks can be maintain for up to 7 days if sealed in foil bags.

Example 1

This example demonstrates how the flux block of the present disclosure can be used to determine correction factors for a flux analyzer. In this example, five flux blocks having the general arrangement of FIG. 1 were evaluated to calculate a sensor correction factor from repeated measurements of the sensor in each well in each flux block. As described above, the correction factor is applied in calibration to calibrate the flux analyzer. By applying a correction factor to calibrate the flux analyzer, the coefficient of variance for the data collected from the sensors improves.

The five flux blocks included 24 wells. Each flux block was evaluated in four trials, for a total of 20 trials. The chamber was filled with 100% CO2 gas, and the wells were loaded with a small volume of phosphate buffered saline. ECAR and OCR data were measured in each well of each flux block using a Seahorse XF24 Analyzer (more particularly, using the fluorescent sensors in that analyzer). The data was further used to calculate a correction factor to be applied for calibrating each sensor of the flux analyzer, as described below.

Data related to calculating the correction factor is listed in Tables 1 through 6B; this data is generally representative of testing and use of the flux block of the present disclosure. In those tables, no recharge refers to a series of tests where the gas in the chamber is not replenished between tests and recharge refers to a series of tests where the gas in the chamber is replenished between tests. As shown in Table 1, the first flux block (labeled FB1) was tested four times. ECAR and OCR data were measured in each of the twenty-four wells in each trial. The same data were collected in each trial when evaluating the other four flux blocks.

TABLE 1

| | Flux Block-1 | | | | | | | |
|---|---|---|---|---|---|---|---|---|
| | NO RECHARGE | | | | RECHARGE | | | |
| | FB1-run1 | | FB1-run2 | | FB1-run3 | | FB1-run4 | |
| WELL | ECAR | OCR | ECAR | OCR | ECAR | OCR | ECAR | OCR |
| 1 | 90 | 506 | 93 | 522 | 76 | 526 | 75 | 495 |
| 2 | 84 | 446 | 79 | 500 | 64 | 488 | 70 | 408 |
| 3 | 84 | 596 | 76 | 488 | 60 | 442 | 66 | 453 |
| 4 | 70 | 512 | 80 | 523 | 63 | 495 | 67 | 489 |
| 5 | 70 | 471 | 77 | 480 | 67 | 449 | 73 | 464 |
| 6 | 79 | 565 | 81 | 514 | 75 | 499 | 73 | 514 |
| 7 | 97 | 545 | 108 | 548 | 93 | 561 | 99 | 549 |
| 8 | 84 | 514 | 81 | 506 | 83 | 487 | 86 | 507 |
| 9 | 82 | 510 | 80 | 514 | 80 | 508 | 89 | 516 |
| 10 | 80 | 516 | 84 | 525 | 90 | 473 | 83 | 515 |
| 11 | 76 | 488 | 83 | 499 | 82 | 534 | 88 | 505 |
| 12 | 71 | 503 | 75 | 519 | 75 | 378 | 75 | 531 |
| 13 | 94 | 486 | 85 | 559 | 84 | 572 | 82 | 549 |

TABLE 1-continued

| | Flux Block-1 | | | | | | | |
|---|---|---|---|---|---|---|---|---|
| | NO RECHARGE | | | | RECHARGE | | | |
| | FB1-run1 | | FB1-run2 | | FB1-run3 | | FB1-run4 | |
| WELL | ECAR | OCR | ECAR | OCR | ECAR | OCR | ECAR | OCR |
| 14 | 80 | 533 | 85 | 540 | 84 | 553 | 86 | 536 |
| 15 | 91 | 501 | 91 | 502 | 88 | 496 | 91 | 503 |
| 16 | 91 | 543 | 92 | 534 | 86 | 553 | 89 | 540 |
| 17 | 78 | 524 | 82 | 523 | 77 | 492 | 80 | 519 |
| 18 | 86 | 509 | 93 | 517 | 86 | 481 | 86 | 512 |
| 19 | 86 | 523 | 91 | 530 | 80 | 536 | 81 | 518 |
| 20 | 79 | 484 | 82 | 505 | 76 | 510 | 81 | 496 |
| 21 | 86 | 607 | 78 | 498 | 73 | 497 | 77 | 506 |
| 22 | 77 | 580 | 79 | 514 | 72 | 524 | 77 | 509 |
| 23 | 69 | 506 | 75 | 512 | 68 | 521 | 69 | 504 |
| 24 | 75 | 476 | 77 | 478 | 74 | 482 | 78 | 485 |
| AVERAGE | 82 | 518 | 84 | 515 | 77 | 502 | 80 | 505 |
| SD | 7.6 | 39.0 | 7.7 | 19.7 | 8.7 | 42.4 | 8.4 | 30.9 |
| % CV | 9% | 8% | 9% | 4% | 11% | 8% | 10% | 6% |

TABLE 2

| | Flux Block-2 | | | | | | | |
|---|---|---|---|---|---|---|---|---|
| | NO RECHARGE | | | | RECHARGE | | | |
| | FB2-run 1 | | FB2-run2 | | FB2-run 3 | | FB2-run4 | |
| WELL | ECAR | OCR | ECAR | OCR | ECAR | OCR | ECAR | OCR |
| 1 | 61 | 455 | 56 | 460 | 75 | 556 | 59 | 431 |
| 2 | 63 | 458 | 67 | 453 | 62 | 449 | 67 | 460 |
| 3 | 65 | 427 | 68 | 423 | 65 | 437 | 64 | 438 |
| 4 | 61 | 459 | 69 | 474 | 58 | 467 | 62 | 482 |
| 5 | 72 | 445 | 72 | 450 | 69 | 457 | 73 | 449 |
| 6 | 83 | 504 | 87 | 505 | 75 | 474 | 77 | 490 |
| 7 | 96 | 535 | 92 | 522 | 91 | 474 | 95 | 484 |
| 8 | 84 | 508 | 88 | 506 | 80 | 577 | 68 | 482 |
| 9 | 81 | 507 | 92 | 506 | 82 | 524 | 85 | 472 |
| 10 | 96 | 515 | 97 | 509 | 92 | 509 | 88 | 507 |
| 11 | 85 | 496 | 94 | 499 | 84 | 540 | 88 | 493 |
| 12 | 78 | 511 | 87 | 523 | 68 | 491 | 73 | 502 |
| 13 | 80 | 551 | 90 | 502 | 77 | 536 | 83 | 511 |
| 14 | 80 | 528 | 88 | 528 | 76 | 504 | 81 | 520 |
| 15 | 88 | 518 | 94 | 517 | 85 | 493 | 89 | 515 |
| 16 | 91 | 555 | 95 | 545 | 90 | 548 | 91 | 549 |
| 17 | 79 | 516 | 83 | 515 | 75 | 505 | 78 | 516 |
| 18 | 92 | 546 | 91 | 536 | 89 | 520 | 93 | 533 |
| 19 | 73 | 506 | 79 | 505 | 72 | 481 | 76 | 474 |
| 20 | 75 | 487 | 80 | 490 | 71 | 465 | 74 | 479 |
| 21 | 75 | 483 | 79 | 477 | 70 | 460 | 73 | 475 |
| 22 | 78 | 499 | 86 | 495 | 75 | 485 | 81 | 460 |
| 23 | 72 | 494 | 79 | 497 | 71 | 481 | 72 | 489 |
| 24 | 76 | 489 | 81 | 488 | 77 | 458 | 73 | 472 |
| AVERAGE | 79 | 500 | 83 | 497 | 76 | 495 | 78 | 487 |
| SD | 10.1 | 33.3 | 10.4 | 29.0 | 9.1 | 36.9 | 10.0 | 28.8 |
| % CV | 13% | 7% | 13% | 6% | 12% | 7% | 13% | 6% |

TABLE 3

| | Flux Block-3 | | | | | | | |
|---|---|---|---|---|---|---|---|---|
| | NO RECHARGE | | | | RECHARGE | | | |
| | FB3-run 1 | | FB3-run 2 | | FB3-run 3 | | FB3-run 4 | |
| WELL | ECAR | OCR | ECAR | OCR | ECAR | OCR | ECAR | OCR |
| 1 | 71 | 517 | 66 | 461 | 74 | 531 | 103 | 506 |
| 2 | 64 | 480 | 51 | 451 | 55 | 447 | 82 | 456 |
| 3 | 68 | 481 | 60 | 452 | 58 | 414 | 97 | 452 |
| 4 | 65 | 514 | 53 | 479 | 54 | 483 | 80 | 470 |

TABLE 3-continued

| | Flux Block-3 | | | | | | | |
|---|---|---|---|---|---|---|---|---|
| | NO RECHARGE | | | | RECHARGE | | | |
| | FB3-run 1 | | FB3-run 2 | | FB3-run 3 | | FB3-run 4 | |
| WELL | ECAR | OCR | ECAR | OCR | ECAR | OCR | ECAR | OCR |
| 5 | 76 | 496 | 69 | 472 | 65 | 483 | 111 | 474 |
| 6 | 76 | 534 | 61 | 507 | 65 | 534 | 106 | 472 |
| 7 | 99 | 525 | 95 | 519 | 85 | 508 | 143 | 520 |
| 8 | 67 | 485 | 66 | 478 | 79 | 503 | 106 | 429 |
| 9 | 65 | 514 | 63 | 508 | 70 | 518 | 110 | 510 |
| 10 | 69 | 505 | 67 | 497 | 69 | 512 | 111 | 402 |
| 11 | 77 | 527 | 80 | 524 | 80 | 528 | 125 | 510 |
| 12 | 84 | 518 | 82 | 518 | 78 | 536 | 121 | 517 |
| 13 | 85 | 527 | 90 | 465 | 75 | 534 | 134 | 527 |
| 14 | 74 | 505 | 75 | 505 | 77 | 542 | 114 | 507 |
| 15 | 73 | 491 | 75 | 494 | 77 | 516 | 115 | 488 |
| 16 | 76 | 504 | 78 | 511 | 80 | 552 | 120 | 514 |
| 17 | 67 | 490 | 68 | 492 | 71 | 523 | 108 | 456 |
| 18 | 85 | 514 | 88 | 514 | 80 | 513 | 137 | 450 |
| 19 | 74 | 513 | 65 | 378 | 72 | 484 | 114 | 511 |
| 20 | 66 | 461 | 64 | 366 | 66 | 503 | 110 | 419 |
| 21 | 61 | 455 | 66 | 433 | 62 | 478 | 101 | 464 |
| 22 | 61 | 476 | 66 | 481 | 64 | 506 | 102 | 435 |
| 23 | 62 | 480 | 66 | 491 | 65 | 515 | 98 | 491 |
| 24 | 67 | 456 | 68 | 457 | 74 | 462 | 96 | 458 |
| AVERAGE | 72 | 499 | 70 | 477 | 71 | 505 | 110 | 477 |
| SD | 9.2 | 23.1 | 11.0 | 40.8 | 8.4 | 32.2 | 15.1 | 35.3 |
| % CV | 13% | 5% | 16% | 9% | 12% | 6% | 14% | 7% |

TABLE 4

| | Flux Block-4 | | | | | | | |
|---|---|---|---|---|---|---|---|---|
| | NO RECHARGE | | | | RECHARGE | | | |
| | FB4-run1 | | FB4-run2 | | FB4-run3 | | FB4-run4 | |
| WELL | ECAR | OCR | ECAR | OCR | ECAR | OCR | ECAR | OCR |
| 1 | 72 | 471 | 77 | 481 | 72 | 497 | 63 | 469 |
| 2 | 60 | 438 | 59 | 439 | 71 | 495 | 51 | 440 |
| 3 | 60 | 430 | 61 | 424 | 75 | 503 | 67 | 411 |
| 4 | 64 | 459 | 57 | 455 | 70 | 505 | 62 | 455 |
| 5 | 78 | 442 | 70 | 454 | 79 | 504 | 74 | 413 |
| 6 | 81 | 503 | 74 | 499 | 79 | 532 | 77 | 510 |
| 7 | 102 | 521 | 106 | 529 | 87 | 526 | 98 | 515 |
| 8 | 81 | 508 | 84 | 510 | 85 | 536 | 85 | 506 |
| 9 | 89 | 512 | 87 | 486 | 85 | 532 | 82 | 492 |
| 10 | 75 | 525 | 82 | 528 | 81 | 536 | 79 | 525 |
| 11 | 83 | 510 | 83 | 430 | 86 | 515 | 84 | 515 |
| 12 | 84 | 515 | 88 | 520 | 76 | 530 | 84 | 515 |
| 13 | 85 | 531 | 86 | 528 | 74 | 490 | 87 | 539 |
| 14 | 83 | 497 | 85 | 488 | 84 | 511 | 85 | 502 |
| 15 | 86 | 486 | 90 | 485 | 86 | 488 | 87 | 478 |
| 16 | 79 | 529 | 83 | 528 | 79 | 548 | 80 | 516 |
| 17 | 80 | 489 | 84 | 485 | 79 | 512 | 79 | 492 |
| 18 | 85 | 514 | 89 | 518 | 74 | 520 | 86 | 527 |
| 19 | 67 | 514 | 72 | 518 | 64 | 531 | 64 | 303 |
| 20 | 77 | 485 | 80 | 483 | 76 | 498 | 79 | 457 |
| 21 | 80 | 483 | 82 | 478 | 71 | 462 | 75 | 336 |
| 22 | 83 | 477 | 85 | 478 | 80 | 499 | 86 | 436 |
| 23 | 74 | 491 | 78 | 490 | 73 | 469 | 74 | 508 |
| 24 | 79 | 493 | 74 | 485 | 69 | 499 | 73 | 489 |
| AVERAGE | 79 | 493 | 80 | 488 | 77 | 510 | 78 | 473 |
| SD | 9.3 | 28.4 | 10.9 | 31.1 | 6.3 | 21.6 | 10.4 | 59.3 |
| % CV | 12% | 6% | 14% | 6% | 8% | 4% | 13% | 13% |

TABLE 5

| | Flux Block-5 | | | | | | | |
|---|---|---|---|---|---|---|---|---|
| | NO RECHARGE | | | | RECHARGE | | | |
| | FB5-RUN 1 | | FB5-RUN 2 | | FB5-RUN 3 | | FB5-RUN 4 | |
| WELL | ECAR | OCR | ECAR | OCR | ECAR | OCR | ECAR | OCR |
| 1 | 80 | 473 | 81 | 479 | 74 | 499 | 71 | 372 |
| 2 | 57 | 440 | 67 | 456 | 66 | 492 | 53 | 424 |
| 3 | 68 | 435 | 69 | 445 | 66 | 481 | 64 | 436 |
| 4 | 67 | 473 | 71 | 477 | 66 | 501 | 59 | 473 |
| 5 | 80 | 461 | 81 | 456 | 74 | 396 | 74 | 449 |
| 6 | 96 | 429 | 102 | 500 | 74 | 506 | 79 | 503 |
| 7 | 102 | 500 | 101 | 494 | 89 | 504 | 94 | 473 |
| 8 | 80 | 474 | 78 | 474 | 78 | 485 | 84 | 477 |
| 9 | 80 | 482 | 77 | 461 | 78 | 506 | 76 | 472 |
| 10 | 77 | 489 | 75 | 481 | 76 | 526 | 77 | 489 |
| 11 | 89 | 467 | 92 | 466 | 86 | 494 | 90 | 476 |
| 12 | 89 | 480 | 97 | 501 | 89 | 514 | 85 | 483 |
| 13 | 110 | 526 | 108 | 529 | 89 | 539 | 104 | 502 |
| 14 | 102 | 514 | 105 | 512 | 92 | 487 | 96 | 498 |
| 15 | 93 | 463 | 96 | 486 | 85 | 438 | 88 | 489 |
| 16 | 90 | 507 | 91 | 482 | 82 | 530 | 83 | 505 |
| 17 | 81 | 491 | 86 | 489 | 79 | 510 | 77 | 463 |
| 18 | 112 | 515 | 113 | 524 | 92 | 517 | 107 | 529 |
| 19 | 104 | 535 | 105 | 545 | 92 | 554 | 99 | 549 |
| 20 | 85 | 493 | 92 | 483 | 76 | 506 | 79 | 485 |
| 21 | 84 | 483 | 90 | 474 | 71 | 482 | 75 | 467 |
| 22 | 79 | 485 | 87 | 490 | 71 | 496 | 76 | 479 |
| 23 | 74 | 478 | 79 | 484 | 68 | 510 | 69 | 490 |
| 24 | 85 | 460 | 89 | 463 | 81 | 448 | 78 | 458 |
| AVERAGE | 86 | 481 | 89 | 486 | 79 | 497 | 81 | 477 |
| SD | 13.6 | 26.8 | 12.8 | 24.2 | 8.7 | 32.9 | 13.3 | 34.8 |
| % CV | 16% | 6% | 14% | 5% | 11% | 7% | 17% | 7% |

TABLE 6

| | AVERAGE ECAR | | | AVERAGE OCR | | | Instrument | | | | Correction factor |
|---|---|---|---|---|---|---|---|---|---|---|---|
| WELL | ECAR | ECAR SD | ECAR % cv | OCR | OCR SD | OCR % cv | ECAR | | OCR | | |
| 1 | 74 | 11 | 15% | 485 | 40 | 8% | −6.05 | −8% | −9 | −2% | 1.081375 |
| 2 | 65 | 10 | 15% | 456 | 24 | 5% | −15.91 | −20% | −38 | −8% | 1.246549 |
| 3 | 68 | 9 | 13% | 454 | 42 | 9% | −12.35 | −15% | −41 | −8% | 1.181338 |
| 4 | 65 | 7 | 11% | 482 | 20 | 4% | −15.43 | −19% | −12 | −2% | 1.237252 |
| 5 | 75 | 10 | 13% | 458 | 25 | 5% | −5.24 | −7% | −36 | −7% | 1.069642 |
| 6 | 80 | 11 | 14% | 505 | 27 | 5% | −0.48 | −1% | 11 | 2% | 1.005985 |
| 7 | 99 | 12 | 12% | 518 | 24 | 5% | 18.18 | 23% | 24 | 5% | 0.815647 |
| 8 | 81 | 8 | 10% | 498 | 29 | 6% | 0.89 | 1% | 4 | 1% | 0.989016 |
| 9 | 82 | 10 | 12% | 502 | 19 | 4% | 1.16 | 1% | 8 | 2% | 0.985784 |
| 10 | 82 | 11 | 13% | 504 | 29 | 6% | 1.96 | 2% | 10 | 2% | 0.976196 |
| 11 | 87 | 10 | 12% | 501 | 27 | 5% | 6.19 | 8% | 7 | 1% | 0.928514 |
| 12 | 83 | 12 | 14% | 505 | 33 | 7% | 2.58 | 3% | 11 | 2% | 0.968956 |
| 13 | 90 | 14 | 16% | 525 | 26 | 5% | 9.68 | 12% | 31 | 6% | 0.89262 |
| 14 | 87 | 11 | 12% | 516 | 19 | 4% | 6.13 | 8% | 22 | 4% | 0.929183 |
| 15 | 88 | 9 | 10% | 492 | 19 | 4% | 7.86 | 10% | −2 | 0% | 0.911027 |
| 16 | 87 | 10 | 11% | 530 | 21 | 4% | 6.94 | 9% | 36 | 7% | 0.920536 |
| 17 | 79 | 8 | 10% | 500 | 19 | 4% | −0.95 | −1% | 6 | 1% | 1.011999 |
| 18 | 93 | 14 | 15% | 516 | 20 | 4% | 12.84 | 16% | 21 | 4% | 0.862335 |
| 19 | 81 | 15 | 18% | 500 | 60 | 12% | 0.99 | 1% | 6 | 1% | 0.987827 |
| 20 | 78 | 10 | 13% | 478 | 34 | 7% | −1.98 | −2% | −16 | −3% | 1.025222 |
| 21 | 76 | 9 | 12% | 475 | 47 | 10% | −3.97 | −5% | −19 | −4% | 1.051868 |
| 22 | 78 | 9 | 12% | 490 | 31 | 6% | −2.20 | −3% | −4 | −1% | 1.028119 |
| 23 | 73 | 8 | 10% | 495 | 14 | 3% | −7.65 | −10% | 1 | 0% | 1.105021 |
| 24 | 77 | 7 | 9% | 473 | 15 | 3% | −3.21 | −4% | −21 | −4% | 1.041572 |
| AVERAGE | 80 | 10 | 13% | 494 | 28 | 6% | | | | | |
| SD | 8 | 2 | | 21 | 11 | | | | | | |
| % CV | 10% | 20% | | 4% | 39% | | | | | | |

TABLE 7A

| | | Original Data | | | | |
|---|---|---|---|---|---|---|
| Well | SCF | FB1-run 1 ECAR | FB1-run 2 ECAR | FB1-run 3 ECAR | FB1-run 4 ECAR | FB2-run 1 ECAR |
| 1 | 1.08137479 | 89.6119617 | 93.2799622 | 76.1785606 | 74.7705956 | 60.9401975 |
| 2 | 1.246549312 | 83.8809812 | 79.242285 | 64.2579312 | 70.0484392 | 63.2933664 |
| 3 | 1.181338446 | 84.1534425 | 75.6403122 | 59.9598305 | 65.8474472 | 65.0643076 |
| 4 | 1.237252005 | 70.3843788 | 79.6535144 | 63.0226751 | 66.8341828 | 60.9303178 |
| 5 | 1.069641504 | 70.0143804 | 76.579838 | 66.8113656 | 72.7658473 | 72.431357 |
| 6 | 1.00598515 | 78.9241038 | 80.5621052 | 74.5257068 | 73.0840322 | 83.4464115 |
| 7 | 0.815646582 | 96.6373607 | 107.739986 | 92.6249142 | 99.326922 | 96.0204549 |
| 8 | 0.98901642 | 84.0563585 | 81.4066769 | 82.7083316 | 86.0272529 | 84.465556 |
| 9 | 0.985784233 | 81.9462732 | 80.3239655 | 80.018464 | 89.4875251 | 81.4343198 |
| 10 | 0.976195694 | 80.483165 | 84.0574369 | 90.0210331 | 82.7399803 | 96.0240378 |
| 11 | 0.928513637 | 75.7725142 | 82.5136745 | 82.0218824 | 87.7643651 | 84.9727228 |
| 12 | 0.968955717 | 70.7506723 | 75.0075889 | 75.0492842 | 75.3755429 | 78.3421352 |
| 13 | 0.892619686 | 93.6566367 | 85.4294639 | 83.7319074 | 82.3164016 | 80.4743018 |
| 14 | 0.929182833 | 79.6736062 | 85.2551379 | 83.9493197 | 85.8965431 | 80.3708037 |
| 15 | 0.911026763 | 90.8479969 | 90.8641234 | 87.8687104 | 90.5704381 | 88.3244069 |
| 16 | 0.920535631 | 91.2749705 | 91.786507 | 86.1715858 | 89.2136009 | 91.3666749 |
| 17 | 1.011999196 | 78.3189936 | 81.5375405 | 77.176296 | 80.3430622 | 78.6484295 |
| 18 | 0.862335474 | 86.4374653 | 92.6708021 | 86.0528466 | 85.7863493 | 92.4808562 |
| 19 | 0.987827409 | 85.8536538 | 90.999879 | 80.0462754 | 81.0017595 | 73.2350313 |
| 20 | 1.025222423 | 79.3133607 | 82.4589641 | 76.379714 | 81.4589362 | 74.5092491 |
| 21 | 1.05186766 | 86.1692893 | 77.7860387 | 73.3345084 | 77.1843288 | 74.7094829 |
| 22 | 1.028118995 | 77.3115065 | 78.5655247 | 71.5917543 | 76.5309262 | 78.4002449 |
| 23 | 1.105020635 | 69.4050541 | 75.1118177 | 68.3691277 | 68.8348972 | 72.2803578 |
| 24 | 1.041572042 | 75.2434173 | 76.933904 | 74.370416 | 78.4870179 | 76.2710909 |
| AVG | | 81.671731 | 83.558627 | 77.343435 | 80.0706831 | 78.6848381 |
| SD | | 7.63926803 | 7.7113534 | 8.72745167 | 8.36532409 | 10.1211856 |
| cv | | 9% | 9% | 11% | 10% | 13% |

| Well | SCF | FB2-run2 ECAR | FB2-run 3 ECAR | FB2-run4 ECAR | FB3-run 1 ECAR | FB3-run 2 ECAR |
|---|---|---|---|---|---|---|
| 1 | 1.08137479 | 56.1588551 | 75.1327384 | 58.9416867 | 71.1566829 | 65.6770873 |
| 2 | 1.246549312 | 67.4488459 | 62.3056134 | 66.6732294 | 63.6031602 | 50.7183271 |
| 3 | 1.181338446 | 68.4291366 | 64.8574085 | 64.4358737 | 67.8719539 | 60.1897486 |
| 4 | 1.237252005 | 69.1377667 | 57.7935972 | 62.4399996 | 65.2058759 | 53.4047157 |
| 5 | 1.069641504 | 72.3842855 | 69.0613433 | 72.5578511 | 76.3309814 | 68.9273837 |
| 6 | 1.00598515 | 87.2129072 | 74.875157 | 76.7470049 | 75.6008541 | 60.7792193 |
| 7 | 0.815646582 | 92.0931333 | 90.8392956 | 95.20618 | 99.1387621 | 95.178036 |
| 8 | 0.98901642 | 87.5730133 | 80.2655954 | 68.1167392 | 67.1516932 | 65.5644437 |
| 9 | 0.985784233 | 91.9546811 | 81.8116704 | 85.0462703 | 64.8361016 | 62.5405687 |
| 10 | 0.976195694 | 97.4176257 | 91.7983697 | 88.4068855 | 68.5520821 | 67.2022214 |
| 11 | 0.928513637 | 93.9082228 | 84.0056715 | 88.3470159 | 76.836607 | 79.7035293 |
| 12 | 0.968955717 | 86.597794 | 68.3312319 | 73.2234336 | 83.997875 | 82.130023 |
| 13 | 0.892619686 | 89.7126493 | 76.6410512 | 83.1575563 | 84.8208929 | 90.4683111 |
| 14 | 0.929182833 | 88.3467996 | 75.5566302 | 80.7380947 | 73.8833611 | 74.5701783 |
| 15 | 0.911026763 | 94.4028144 | 85.3054246 | 88.5909089 | 72.8718058 | 74.7580481 |
| 16 | 0.920535631 | 95.0755612 | 90.3808473 | 91.3586156 | 76.0557461 | 78.2777678 |
| 17 | 1.011999196 | 83.2162726 | 75.1680815 | 77.8584215 | 66.630164 | 67.62361 |
| 18 | 0.862335474 | 91.2319292 | 89.4419615 | 93.16771 | 85.3966779 | 88.178782 |
| 19 | 0.987827409 | 78.9930539 | 71.7333066 | 76.405514 | 73.9801636 | 64.5725623 |
| 20 | 1.025222423 | 79.8600805 | 70.6861577 | 74.2407193 | 65.7041797 | 64.3729294 |
| 21 | 1.05186766 | 79.0960424 | 70.2139832 | 72.7722094 | 61.3507734 | 65.5850265 |
| 22 | 1.028118995 | 85.7199015 | 75.3111771 | 81.0573868 | 61.3435337 | 66.0635305 |
| 23 | 1.105020635 | 79.3086294 | 70.7077754 | 71.682521 | 62.3591741 | 65.5200248 |
| 24 | 1.041572042 | 81.2880311 | 77.3819987 | 72.8542223 | 66.9195309 | 67.6667386 |
| AVG | | 83.1903347 | 76.233587 | 77.6677521 | 72.149943 | 69.9863672 |
| SD | | 10.4305738 | 9.14230864 | 10.0048931 | 9.18148363 | 11.0244694 |
| cv | | 13% | 12% | 13% | 13% | 16% |

| Well | FB3-RUN 3 ECAR | FB3-run 4 ECAR | FB4-run 1 ECAR | FB4-run 2 ECAR | FB4-run 3 ECAR |
|---|---|---|---|---|---|
| 1 | 73.5819468 | 102.555301 | 72.3554283 | 77.4656697 | 71.6975336 |
| 2 | 54.5400221 | 82.3817909 | 59.959784 | 58.53901 | 70.5365292 |
| 3 | 58.2609501 | 97.0081679 | 60.3590924 | 61.3997202 | 74.8820654 |
| 4 | 53.8193107 | 79.9792709 | 64.430667 | 56.9545998 | 70.3870113 |
| 5 | 64.7887792 | 111.438502 | 78.2202028 | 69.8755956 | 79.0004399 |
| 6 | 64.5369706 | 106.453367 | 81.1811988 | 73.5420132 | 79.4937284 |
| 7 | 84.8935328 | 142.592786 | 102.404989 | 106.400201 | 86.6505707 |
| 8 | 78.562686 | 105.539463 | 81.2048116 | 83.5546907 | 85.4924099 |
| 9 | 69.8505069 | 109.656435 | 89.3361486 | 86.6547873 | 85.1942636 |
| 10 | 68.6920947 | 111.385816 | 75.4889916 | 82.0385236 | 80.7402025 |
| 11 | 79.5522445 | 124.667116 | 82.5846554 | 83.0226854 | 86.3246186 |
| 12 | 77.9399721 | 121.248498 | 84.0723 | 88.4242454 | 76.2434272 |
| 13 | 75.1200352 | 133.889589 | 85.3050788 | 86.3041531 | 73.9102549 |

TABLE 7A-continued

| | Original Data | | | | |
|---|---|---|---|---|---|
| 14 | 77.3311219 | 114.265533 | 83.0977412 | 85.3443203 | 83.6844502 |
| 15 | 76.7204194 | 114.571142 | 86.2439064 | 89.6915918 | 86.3239479 |
| 16 | 80.1857194 | 119.570899 | 79.4346809 | 82.5091355 | 78.6073881 |
| 17 | 71.2526522 | 108.140553 | 79.673299 | 84.3965913 | 79.2321067 |
| 18 | 79.8958466 | 137.389916 | 84.6661305 | 89.3219998 | 74.3810941 |
| 19 | 72.3839789 | 113.562541 | 67.2691703 | 71.5357789 | 63.674902 |
| 20 | 66.4169037 | 109.591394 | 77.168433 | 80.2854161 | 76.1385397 |
| 21 | 62.134004 | 101.057261 | 80.0349645 | 81.6168517 | 71.3437567 |
| 22 | 63.9522025 | 102.480455 | 83.0178199 | 85.0823194 | 79.5545094 |
| 23 | 64.8115167 | 98.1244171 | 73.7679412 | 78.0940309 | 73.218805 |
| 24 | 73.8784761 | 95.9313694 | 78.8974519 | 73.87523 | 68.5678444 |
| AVG | 70.5459122 | 110.145066 | 78.757287 | 79.8303816 | 77.30335 |
| SD | 8.44360642 | 15.1394126 | 9.34393492 | 10.9182734 | 6.31712316 |
| cv | 12% | 14% | 12% | 14% | 8% |

| Well | FB4-run4 ECAR | FB5-RUN 1 ECAR | FB5-RUN 2 ECAR | FB5-RUN 3 ECAR | FB5-RUN 4 ECAR | |
|---|---|---|---|---|---|---|
| 1 | 62.6733667 | 79.866209 | 80.9837313 | 74.1625121 | 70.74534245 | |
| 2 | 51.3756605 | 57.074072 | 66.6736016 | 65.5061887 | 52.61705134 | |
| 3 | 67.0835841 | 67.7018077 | 69.3153772 | 66.0261142 | 63.5414535 | |
| 4 | 61.7608113 | 67.4605446 | 71.0703069 | 66.3737943 | 59.43206043 | |
| 5 | 74.3404551 | 79.6305836 | 81.0576455 | 74.2463687 | 73.79386667 | |
| 6 | 76.6938975 | 96.3071195 | 102.479138 | 73.5827081 | 79.41524936 | |
| 7 | 98.3405728 | 102.221165 | 101.347971 | 88.8724915 | 94.15815128 | |
| 8 | 85.4184732 | 79.5579415 | 78.4666363 | 77.8841039 | 83.86793954 | |
| 9 | 82.438494 | 79.7317997 | 76.5911639 | 77.505448 | 75.86015561 | |
| 10 | 78.6794401 | 76.9710306 | 75.1209524 | 75.9298907 | 76.50149623 | |
| 11 | 84.330193 | 88.8413032 | 91.512032 | 86.1356642 | 90.07737707 | |
| 12 | 83.6347938 | 89.0131159 | 96.7849441 | 89.1415339 | 85.25849586 | |
| 13 | 87.1740917 | 109.522501 | 107.749657 | 89.0153038 | 104.177254 | |
| 14 | 85.471893 | 102.07173 | 104.57063 | 91.8996175 | 95.66855336 | |
| 15 | 87.4771206 | 93.4243242 | 95.7650707 | 85.4220734 | 86.11218074 | |
| 16 | 80.1033755 | 89.5696231 | 91.3921089 | 82.4366455 | 83.14111306 | |
| 17 | 78.8477774 | 80.8680884 | 85.6214254 | 78.6574234 | 76.72703379 | |
| 18 | 86.11092 | 111.995152 | 112.627204 | 91.5878963 | 107.0599494 | |
| 19 | 64.2319373 | 103.514431 | 105.071175 | 91.7549697 | 99.02295584 | |
| 20 | 78.515028 | 85.3738441 | 91.6260466 | 76.1109336 | 79.22011684 | |
| 21 | 75.0550934 | 83.6297192 | 89.7746031 | 71.3634808 | 75.46371056 | |
| 22 | 86.1638499 | 78.9725246 | 87.386753 | 70.7966719 | 75.70671598 | |
| 23 | 74.4262501 | 73.6899927 | 79.4117136 | 68.1261926 | 68.84546351 | |
| 24 | 73.379613 | 84.6384427 | 89.1927467 | 80.7728579 | 78.24509466 | OVERALL |
| AVG | 77.6552788 | 85.901961 | 88.8205264 | 78.8879535 | 80.61078255 | 80.45079 |
| SD | 10.4249862 | 13.5760837 | 12.7920993 | 8.71123946 | 13.32294008 | 10.066901 |
| cv | 13% | 16% | 14% | 11% | 17% | 12% |

TABLE 7B

| | Corrected data using well correction factor | | | | |
|---|---|---|---|---|---|
| Well | FB1-run1 | FB1-run2 | FB1-run3 | FB1-run4 | FB2-run 1 |
| 1 | 96.9041163 | 100.8706 | 82.377575 | 80.8550371 | 65.8991933 |
| 2 | 104.561779 | 98.7794159 | 80.1006799 | 87.3188337 | 78.8983023 |
| 3 | 99.4136969 | 89.3568089 | 70.832853 | 77.7881209 | 76.862968 |
| 4 | 87.0832137 | 98.5514703 | 77.9749311 | 82.6907266 | 75.3861579 |
| 5 | 74.8902871 | 81.912973 | 71.4642096 | 77.8333703 | 77.4755856 |
| 6 | 79.3964763 | 81.0442814 | 74.9717543 | 73.521451 | 83.9458507 |
| 7 | 78.821933 | 87.8777515 | 75.5491947 | 81.0156645 | 78.3187559 |
| 8 | 83.1331188 | 80.5125402 | 81.7998981 | 85.0823657 | 83.5378219 |
| 9 | 80.7813441 | 79.1820988 | 78.8809402 | 88.2153914 | 80.2766685 |
| 10 | 78.5673191 | 82.056508 | 87.8781448 | 80.7704124 | 93.7382522 |
| 11 | 70.3558127 | 76.6150719 | 76.1584363 | 81.4904098 | 78.8983318 |
| 12 | 68.5542684 | 72.6790321 | 72.7194329 | 73.0355632 | 75.9100597 |
| 13 | 83.5997576 | 76.2560213 | 74.7407489 | 73.4772406 | 71.8329461 |
| 14 | 74.0313472 | 79.2176106 | 78.0042667 | 79.8135933 | 74.6791711 |
| 15 | 82.7649565 | 82.7796482 | 80.0507468 | 82.512093 | 80.4658985 |
| 16 | 84.0218626 | 84.4927502 | 79.3240151 | 82.1242984 | 84.1062797 |
| 17 | 79.2587585 | 82.5159254 | 78.1023495 | 81.3071143 | 79.5921474 |
| 18 | 74.5380926 | 79.9133201 | 74.2064222 | 73.9766121 | 79.7495229 |
| 19 | 84.8085924 | 89.8921747 | 79.0719048 | 80.0157582 | 72.3435713 |
| 20 | 81.3138358 | 84.5387789 | 78.3061954 | 83.5135279 | 76.3885529 |
| 21 | 90.6386887 | 81.8206185 | 77.1381977 | 81.1876993 | 78.5844889 |
| 22 | 79.4854284 | 80.7747083 | 73.6048425 | 78.6828989 | 80.604781 |

TABLE 7B-continued

Corrected data using well correction factor

| | | | | | |
|---|---|---|---|---|---|
| 23 | 76.6940169 | 83.0001085 | 75.5492969 | 76.0639817 | 79.8712868 |
| 24 | 78.3714398 | 80.1322035 | 77.4621461 | 81.7498835 | 79.4418359 |
| AVG | 82.166256 | 83.9488508 | 77.3445493 | 80.1684187 | 78.6170179 |
| SD | 8.65394573 | 7.1109348 | 3.76007064 | 4.08350793 | 5.17517019 |
| cv | 11% | 8% | 5% | 5% | 7% |

| Well | FB2-run2 | FB2-run 3 | FB2-run4 | FB3-run 1 | FB3-run 2 |
|---|---|---|---|---|---|
| 1 | 60.7287702 | 81.2466491 | 63.7380541 | 76.947043 | 71.0215465 |
| 2 | 84.0783124 | 77.6670195 | 83.1114683 | 79.2844757 | 63.2228957 |
| 3 | 80.8379699 | 76.6185502 | 76.1205749 | 80.1797485 | 71.1044641 |
| 4 | 85.5408405 | 71.505244 | 77.2540147 | 80.6761007 | 66.0750915 |
| 5 | 77.425236 | 73.8708791 | 77.610889 | 81.6467857 | 73.7275904 |
| 6 | 87.7348895 | 75.323296 | 77.2063472 | 76.0533366 | 61.142992 |
| 7 | 75.1154494 | 74.092761 | 77.6545953 | 80.8621925 | 77.6316397 |
| 8 | 86.6111481 | 79.3839919 | 67.3685735 | 66.4141272 | 64.8443114 |
| 9 | 90.6474748 | 80.6486547 | 83.8372724 | 63.9144067 | 61.6515066 |
| 10 | 95.0986667 | 89.6131732 | 86.3024209 | 66.9202473 | 65.6025192 |
| 11 | 87.1950655 | 78.0004115 | 82.031409 | 71.3438374 | 74.0058138 |
| 12 | 83.9094276 | 66.2099378 | 70.9502646 | 81.3902211 | 79.5803553 |
| 13 | 80.0792769 | 68.4113111 | 74.2280718 | 75.7127988 | 80.7537955 |
| 14 | 82.0903296 | 70.2059237 | 75.0204516 | 68.6511509 | 69.2893296 |
| 15 | 86.0034904 | 77.7155248 | 80.7066889 | 66.3881654 | 68.1065825 |
| 16 | 87.5204417 | 83.1987903 | 84.0988609 | 70.0120242 | 72.0574744 |
| 17 | 84.2148009 | 76.070038 | 78.7926599 | 67.4296724 | 68.4350389 |
| 18 | 78.6725289 | 77.1289762 | 80.3418214 | 73.6405846 | 76.0396917 |
| 19 | 78.0315037 | 70.8601264 | 75.4754609 | 73.0796333 | 63.786547 |
| 20 | 81.8743452 | 72.4690338 | 76.1132502 | 67.3613983 | 65.9965706 |
| 21 | 83.198569 | 73.8558182 | 76.5467336 | 64.5328944 | 68.9867683 |
| 22 | 88.130259 | 77.4288517 | 83.336639 | 63.0684523 | 67.9211706 |
| 23 | 87.637672 | 78.1335509 | 79.2106649 | 68.9081741 | 72.4009793 |
| 24 | 84.6673405 | 80.5989264 | 75.8829211 | 69.7015124 | 70.479783 |
| AVG | 83.2101587 | 76.2607267 | 77.6225878 | 72.2549576 | 69.7443524 |
| SD | 6.57679685 | 5.08427951 | 5.24738619 | 6.16531811 | 5.37680325 |
| cv | 8% | 7% | 7% | 9% | 8% |

| Well | FB3-RUN 3 | FB3-run 4 | FB4-run1 | FB4-run2 | FB4-run3 |
|---|---|---|---|---|---|
| 1 | 79.5696622 | 110.900717 | 78.2433361 | 83.7694223 | 77.5319054 |
| 2 | 67.9868271 | 102.692965 | 74.7428276 | 72.9917762 | 87.927262 |
| 3 | 68.8259002 | 114.599478 | 71.3045164 | 72.5338501 | 88.4610627 |
| 4 | 66.58805 | 98.9545133 | 79.716972 | 70.4671928 | 87.0864708 |
| 5 | 69.3007672 | 119.199247 | 83.6675754 | 74.7418372 | 84.5021493 |
| 6 | 64.923234 | 107.090507 | 81.6670805 | 73.9821731 | 79.9695103 |
| 7 | 69.2431199 | 116.305319 | 83.5262793 | 86.7849603 | 70.6762418 |
| 8 | 77.6997865 | 104.380262 | 80.3128921 | 82.6369611 | 84.4533972 |
| 9 | 68.8575284 | 108.097585 | 88.0661667 | 85.4229231 | 83.9831618 |
| 10 | 67.056927 | 108.734354 | 73.6920286 | 80.0856535 | 78.818238 |
| 11 | 73.8653438 | 115.755117 | 76.6809788 | 77.0876956 | 80.1535855 |
| 12 | 75.5203816 | 117.484425 | 81.4623357 | 85.6791781 | 73.8765046 |
| 13 | 67.0536223 | 119.512483 | 76.1449927 | 77.0367861 | 65.9737486 |
| 14 | 71.854751 | 106.173572 | 77.2129946 | 79.3004774 | 77.7581545 |
| 15 | 69.8943553 | 104.377376 | 78.5705069 | 81.7114405 | 78.6434268 |
| 16 | 73.8138118 | 110.069273 | 73.1224541 | 75.9525991 | 72.3609016 |
| 17 | 72.1076267 | 109.438153 | 80.6293145 | 85.4092826 | 80.1828282 |
| 18 | 68.8970227 | 118.476198 | 73.0106077 | 77.025529 | 64.141456 |
| 19 | 71.5028783 | 112.180191 | 66.4503302 | 70.6650011 | 62.8998135 |
| 20 | 68.092099 | 112.355555 | 79.1148079 | 82.3104088 | 78.0589381 |
| 21 | 65.3567494 | 106.298865 | 84.1861908 | 85.8501268 | 75.0441903 |
| 22 | 65.7504742 | 105.362103 | 85.3521976 | 87.4747488 | 81.7915023 |
| 23 | 71.6180633 | 108.429506 | 81.5150972 | 86.2955156 | 80.9082904 |
| 24 | 76.9497552 | 99.9194323 | 82.1773801 | 76.9463741 | 71.4183497 |
| AVG | 70.5136974 | 109.866133 | 78.7737443 | 79.6725792 | 77.7800454 |
| SD | 4.02488381 | 5.94987991 | 5.00391642 | 5.48861987 | 7.12341778 |
| cv | 6% | 5% | 6% | 7% | 9% |

| Well | FB4-run4 | FB5-RUN 1 | FB5-RUN 2 | FB5-RUN3 | FB5-RUN4 |
|---|---|---|---|---|---|
| 1 | 67.7733987 | 86.365305 | 87.5737654 | 80.197471 | 76.50222982 |
| 2 | 64.0422943 | 71.1456452 | 83.2365872 | 81.6566945 | 65.58974917 |
| 3 | 79.248417 | 79.9787483 | 81.88492 | 77.9991871 | 75.06396191 |
| 4 | 76.4136876 | 83.4656941 | 87.9318797 | 82.1211101 | 73.53243591 |
| 5 | 79.5176361 | 85.1761772 | 86.7026218 | 79.4169975 | 78.93298251 |
| 6 | 77.1529219 | 96.883532 | 103.092491 | 74.0231116 | 79.89056151 |
| 7 | 80.2111521 | 83.3763436 | 82.6641258 | 72.4885439 | 76.79977427 |
| 8 | 84.4802726 | 78.6841105 | 77.6047918 | 77.0286577 | 82.94676936 |
| 9 | 81.2665676 | 78.5983511 | 75.5023618 | 76.4036486 | 74.78174533 |
| 10 | 76.8065306 | 75.1387886 | 73.3327502 | 74.1224323 | 74.68043118 |

TABLE 7B-continued

Corrected data using well correction factor

| | | | | | | |
|---|---|---|---|---|---|---|
| 11 | 78.3017342 | 82.4903615 | 84.9701696 | 79.9781388 | 83.63807295 | |
| 12 | 81.0384116 | 86.2497675 | 93.7803249 | 86.3741989 | 82.61170696 | |
| 13 | 77.8133104 | 97.7619401 | 96.1794649 | 79.4568126 | 92.99066778 | |
| 14 | 79.4190157 | 94.8432991 | 97.1652341 | 85.391547 | 88.89357748 | |
| 15 | 79.693998 | 85.1120596 | 87.2445423 | 77.821795 | 78.45050126 | |
| 16 | 73.7380113 | 82.4520295 | 84.1296927 | 75.8858695 | 76.53435698 | |
| 17 | 79.7938873 | 81.8384404 | 86.6488137 | 79.6012492 | 77.6476965 | |
| 18 | 74.256501 | 96.577392 | 97.1224336 | 78.979492 | 92.32159217 | |
| 19 | 63.4500682 | 102.254392 | 103.792186 | 90.638074 | 97.81758991 | |
| 20 | 80.4953672 | 87.5271793 | 93.9370775 | 78.0306357 | 81.21824012 | |
| 21 | 78.9480254 | 87.967397 | 94.4310017 | 75.0649376 | 79.37783662 | |
| 22 | 88.5866908 | 81.1931526 | 89.8439807 | 72.7874031 | 77.83551278 | |
| 23 | 82.2425421 | 81.4289625 | 87.7515822 | 75.2808486 | 76.07565777 | |
| 24 | 76.4301533 | 88.1570356 | 92.9006713 | 84.1307505 | 81.49790301 | OVERALL |
| AVG | 77.5466915 | 85.6110877 | 88.7259779 | 78.953317 | 80.23464805 | 80.45079 |
| SD | 5.75419702 | 7.52585143 | 7.89195843 | 4.46926259 | 7.04553136 | 5.8755866 |
| cv | 7% | 9% | 9% | 6% | 9% | 7% |

Upon collecting all ECAR and OCR data for each trial of each flux block, the average ECAR and OCR for each well of all five flux blocks were calculated. This data is represented as "AVG" in Table 6. For example, the average ECAR measurement for well 1 in the five flux blocks evaluated was 74. The average ECAR measurement and the average OCR measurement were calculated for each well across the five flux blocks. In this manner, an average sensor measurement can be obtained for a given sensor, by repeated measurements with a single flux block or multiple measurements with several flux blocks.

To calculate a sensor correction factor, the average ECAR and OCR measurements from each sensor (that is, from wells in the same position across all five flux blocks) were calculated. These measurements were calculated by averaging each average ECAR and OCR reading of each well (well 1, well 2, . . . well 24) of the five flux blocks. Additionally, the standard deviation of ECAR and OCR measurements across all wells of a flux block as calculated from each ECAR and OCR average reading for each well of the five flux blocks. The same sensor was used in the same well of all five flux blocks; for example, sensor 24 of the analyzer was used to measure ECAR and OCR in well 24 in each of the five flux blocks. The average ECAR and OCR and the standard deviation for ECAR and OCR measurements were used to calculate the coefficient of variation of ECAR and OCR for any flux block. As seen in Table 6, the coefficient of variation for ECAR measurements was 10% and the CV for OCR measurements was 4%. This data shows good interwell reproducibility of ECAR and OCR measurements amongst the five flux blocks.

Furthermore, a correction factor for each well of a flux block was calculated by dividing the average ECAR measurement of a flux block by the average ECAR among the measurements from each sensor in the analyzer. As seen in Table 7A, the average coefficient of variation was calculated from the coefficients of variation of each of the flux blocks. This average CV was 12. Furthermore, Table 7B shows how the CV decreases, and therefore the reproducibility of results improves, when applying the correction factor to data collected from using the flux block. In Table 7B the correction factor was used as a multiplier by the average ECAR measurement from each well of a flux block to equate to a calibrated average ECAR measurement from each well of a flux block. The average ECAR measurement of each well of a flux block was adjusted in this manner. Furthermore, the corrected average ECAR measurement of each well of a flux block was averaged to equate to an average coefficient of variation of 7%. Thus, by applying the correction factor, the average coefficient of variation of the 24-sensor analyzer was lowered by 5%, thus showing that applying the correction factor when calibrating the flux analyzer provides improved results.

Example 2

This example compares a flux block of the present disclosure to a biological (cell-based) standard in taking measurements from a flux analyzer. In this example, the flux blocks had the general arrangement of FIG. 1, though some flux blocks had 96 wells. A flux block and a cell-based standard were each used to obtain OCR and ECAR measurements from Seahorse XF24 and XF96 flux analyzers. The cell-based standard was a confluent monolayer of cells (C2C12 skeletal mouse fibroblasts). Table 8A shows data from the XF24 analyzers, and Table 8B shows data from the XF96 analyzers; this data is generally representative of testing and use of the flux block of the present disclosure. The tables report the coefficients of variance (CV) among wells of the standards (which is the CV for the sensors of the analyzer used with those wells). The rates/flux of OCR and ECAR measured by each analyzer (calculated from all 24 or 96 sensors of the analyzer) are also next. For OCR the CV between the different well plates is calculated, and is 39% when the cell-based standards were used but only 18% when the flux blocks were used. For ECAR, the CV was 34% for cell-based standards and 22% for the flux blocks. Thus, the flux blocks produced measurements having far less variation due to the standard (as opposed to variation attributable to the analyzer) than the cell-based standards.

TABLE 8A

| XF24 | Cell-Based Standard | Flux Block |
|---|---|---|
| Average OCR (all plates) | 211 | 496 |
| CV OCR (interwell variance within a plate) | 10% | 7% |
| CV OCR Average | 39% | 18% |
| Average ECAR | 54 | 73 |
| CV ECAR | 8% | 13% |
| CV ECAR (variance between all plates) | 34% | 22% |

TABLE 8B

| XF96 | Cell-Based Standard | Flux Block |
|---|---|---|
| Average OCR (all plates) | 158 | 142 |
| CV OCR (interwell within a plate) | 5% | 9% |
| Unit OCR (variance of all plates) | 30% | 23% |
| Average ECAR (all plates) | 46 | 66 |
| CV ECAR (interwell within a plate) | 11% | 9% |
| Unit ECAR (variance between all plates) | 22% | 18% |

With regard to interwell variance (that is, the CV from the 24 or 96 measurements of the individual wells of a single well-plate), some of the measurements using the flux blocks resulted in higher CV numbers than the cell-based standards. For the XF24 analyzers, the CV % of ECAR was 8% for the cell-based assay and 13% for the flux blocks. For the XF96 analyzers, the CV % of OCR was 5% for the cell-based standard and 9% for the flux blocks. However, at least some of this variance is attributed to the sensors rather than the standards.

All of the references cited herein, including patents, patent applications, and publications, are hereby incorporated in their entireties by reference.

In the present disclosure, wherever the word "comprising" is found, it is contemplated that the words "consisting essentially of" or "consisting of" may be used in its place. Use of the singular includes the plural except where specifically indicated. Whenever the term "about" appears before a value, it should be understood that the specification is also providing a description of that value apart from the term "about", and vice versa.

In the present disclosure, any of the functions recited herein may be performed by one or more means for performing such functions. With respect to the processes described in the specification, it is intended that the specification also provides a description of the apparatus for performing those processes. With respect to the apparatus described in the specification, it is intended that the specification also provides a description of the components, parts, portions, of such apparatus.

Although the dependent claims have single dependencies in accordance with U.S. patent practice, each of the features in any of the dependent claims can be combined with each of the features of other dependent claims or the main claim.

It should be understood that various changes and modifications to the presently preferred embodiments described herein will be apparent to those skilled in the art. Such change and modifications can be made without departing from the spirit and scope of the present subject matter and without diminishing its intended advantages. It is therefore intended that such changes and modifications be covered by the appended claims.

I claim:

1. An apparatus for calibrating a flux analyzer comprising:
   a first frame comprising a plurality of wells, each well having a well opening at its bottom;
   a second frame connected or integrally formed with the first frame wherein the second frame defines a chamber and an inlet to the chamber, and the second frame has at least one chamber opening, wherein the chamber opening at least partially overlaps the well openings; and
   a selectively permeable membrane between the first and second frames that separates the well openings from the chamber opening, wherein the membrane is substantially impermeable to water;
   wherein the second frame comprises a removable or slidable wall opposite the first frame and adapted to allow access to the chamber.

2. The apparatus of claim 1, wherein the membrane is substantially permeable to O2, CO2, or both.

3. The apparatus of claim 1, wherein the chamber opening is a plurality of chamber openings and each of the well openings is aligned with a chamber opening.

4. The apparatus of claim 1, wherein further comprising a first separator on a first side of the membrane, and a second separator on a second side of the membrane, and both of the separators comprise separator openings, and the first and second separators fit between the first and second frames and are positioned so that the separator openings align with the well openings and the chamber opening.

5. The apparatus of claim 1, wherein the wells have a conical shape at least partially along a depth of the well.

6. The apparatus of claim 1, wherein the first frame has a bottom wall at the bottom of each of the wells, and each of the bottom walls circumscribes one of the well openings, and each of the bottom walls of the wells has one or more sensor stops.

7. The apparatus of claim 1, wherein the membrane is physically or chemically fastened to one or both of the frames.

8. The apparatus of claim 1, wherein the membrane is removable from the apparatus, so that it can be replaced, thereby rejuvenating the calibration apparatus.

9. A method of calibrating a flux analyzer comprising:
   filling the plurality of wells of an apparatus with a test solution, wherein the test solution contains a first analyte having a known value, and the apparatus comprises:
      a first frame comprising a plurality of wells, each well having a well opening at its bottom;
      a second frame connected or integrally formed with the first frame wherein the second frame defines a chamber and an inlet to the chamber, and the second frame has at least one chamber opening, wherein the chamber opening at least partially overlaps the well openings; and
      a selectively permeable membrane between the first and second frames that separates the well openings from the chamber opening;
   contacting the test solution with a flux sensor that measures the first analyte;
   supplying a test fluid to the chamber of the second frame of the apparatus, wherein the test fluid contains a substance that crosses the membrane;
   measuring flux of the first analyte to obtain a measured flux.

10. The method of claim 9, adjusting the flux analyzer based at least partially on the measured flux, or adjusting the measured flux to obtain a corrected measured flux.

11. The method of claim 10, wherein the step of measuring flux comprises measuring flux of the first analyte in more than one of the plurality of wells to obtain a plurality of well flux measurements, calculating an average of the plurality of well flux measurements, calculating well correction factors by dividing the average by the well flux measurements, and the step of adjusting the measured flux comprises multiplying the well flux measurements by the well correction factor.

12. The method of claim 9, wherein the first analyte is H+ and the measured flux is ECAR.

13. The method of claim 9, further comprising measuring flux of a second analyte simultaneously with measuring flux of the first analyte, and the second analyte is O2 and the measured flux is OCR.

14. The method of claim 9, wherein the comparing comprises determining a first correction factor for the first analyte that substantially converts measured flux to calculated flux.

15. The method of claim 14, further comprising using the first correction factor to adjust the flux analyzer or in software associated with the flux analyzer.

16. The method of claim 9, wherein the first analyte is measured in a plurality of wells, and the measured flux comprises individual flux measurements for each of the wells.

17. The method of claim 9, wherein the substance crosses the membrane and changes the first analyte at a calculated flux, and the method comprises comparing the measured flux to the calculated flux; and adjusting the flux analyzer at least partially based on the comparison of the measured flux to the calculated flux.

18. A method of making an apparatus for calibrating a flux analyzer, the method comprising:
  providing a membrane, a first frame and a second frame;
   a first frame comprising a plurality of wells, each well having a well opening at its bottom;
   a second frame that defines a chamber and an inlet to the chamber, and the second frame has a chamber opening; and
   a selectively permeable membrane, wherein the membrane is substantially impermeable to water;
  aligning the well openings to at least partially overlap the chamber opening;
  placing the membrane between the first and second frames to separate the well openings from the frame opening;
  fastening the membrane between the first and second frames;
  wherein the step of providing a membrane comprises:
   determining a desired flux rate of a first analyte through the membrane;
   selecting membrane parameters to obtain the desired flux rate of the first analyte across the permeable membrane; and
   selecting a membrane having the membrane parameters to provide the desired flux rate.

19. The method of claim 18,
wherein the membrane parameters at least include material and thickness, where the desired flux rate is defined by the formula $$Q = \frac{KAdP1dP2}{t},$$

where Q is the desired flux rate; t is thickness of the membrane; A is surface area of the membrane over each of the well openings; dP1 is differential concentration of gas and/or liquid samples across the permeable membrane; dP2 is gas pressure of the test fluid in the chamber of the second frame; and K is a permeation coefficient of the permeable membrane.

* * * * *